United States Patent
Li et al.

(10) Patent No.: US 9,487,469 B2
(45) Date of Patent: Nov. 8, 2016

(54) PROCESS FOR PURIFICATION OF METHYL METHACRYLATE USING MOLECULAR SIEVE MEMBRANES

(71) Applicants: Shiguang Li, Mount Prospect, IL (US); Shaojun Zhou, Palatine, IL (US); Miao Yu, Pittsford, NY (US)

(72) Inventors: Shiguang Li, Mount Prospect, IL (US); Shaojun Zhou, Palatine, IL (US); Miao Yu, Pittsford, NY (US)

(73) Assignees: Gas Technology Institute, Des Plaines, IL (US); The Regents of the University of Colorado, Denver, CO (US)

( * ) Notice: Subject to any disclaimer, the term of this patent is extended or adjusted under 35 U.S.C. 154(b) by 0 days.

(21) Appl. No.: 13/963,677

(22) Filed: Aug. 9, 2013

(65) Prior Publication Data

US 2015/0045579 A1    Feb. 12, 2015

(51) Int. Cl.
C07C 67/56    (2006.01)

(52) U.S. Cl.
CPC .................................... *C07C 67/56* (2013.01)

(58) Field of Classification Search
CPC ..................................................... C07C 67/56
USPC ....................................................... 560/218
See application file for complete search history.

(56) References Cited

U.S. PATENT DOCUMENTS

| | | | |
|---|---|---|---|
| 5,028,735 A | 7/1991 | Segawa et al. | |
| 5,435,892 A | 7/1995 | Miyazaki et al. | |
| 6,107,515 A * | 8/2000 | Yamaguchi et al. | 560/261 |
| 6,211,270 B1 * | 4/2001 | Friedrich et al. | 524/213 |
| 2002/0014457 A1 * | 2/2002 | Coker et al. | 210/644 |
| 2010/0144931 A1 * | 6/2010 | Balduf | 524/27 |

FOREIGN PATENT DOCUMENTS

JP    H08318141    * 3/1996

OTHER PUBLICATIONS

Zhou et al., "Optimization of NaY zeolite membrane preparation for the separation of methanol/methyl methacrylate mixtures," Desalination, 291, 41-47, 2012.*
Shu, et al., "High-Flux MFI Zeolite Membrane Supported on YSZ Hollow Fiber for Separation of Ethanol/Water," Ind. Eng. Chem. Res., 2012, 51, 12073-12080.*
Kusumaningtyas, "Effect of Zeolite 4A on water concentration in the system of the esterification reaction of acetic acid with 1-butanol," Indo. J. Chem., 2006(2), 132-137.*
English translation of JPH08318141, Mar. 12, 1996, pp. 1-12.*

* cited by examiner

*Primary Examiner* — Paul A Zucker
*Assistant Examiner* — Mark Luderer
(74) *Attorney, Agent, or Firm* — Pauley Erickson & Kottis

(57) ABSTRACT

A method for separating the components of a mixture containing methyl methacrylate, water, and methanol in which the mixture is dehydrated in a first stage membrane unit, producing a dehydrated mixture. Methanol in the dehydrated mixture is removed in a second stage membrane unit, producing a retentate stream containing methyl methacrylate and substantially no said methanol.

13 Claims, 2 Drawing Sheets

PROCESS FOR PURIFICATION OF METHYL METHACRYLATE USING MOLECULAR SIEVE MEMBRANES

BACKGROUND OF THE INVENTION

1. Field of the Invention

This invention relates to a method and system for producing methyl methacrylate. In one aspect, this invention relates to the purification of methyl methacrylate. In another aspect, this invention relates to the recovery of methanol in the production of methyl methacrylate. In another aspect, this invention relates to the use of membrane technology for purification of methyl methacrylate. In yet another aspect, this invention relates to the use of molecular sieve membranes for purification of methyl methacrylate.

2. Description of Related Art

Methyl methacrylate (MMA) is by far the most important methacrylic acid ester and is widely used for producing acrylic plastics, e.g., polymethyl methacrylate, and polymer dispersions for paints and coatings. In 2008, over 20% of the world consumption of MMA was MMA produced in the United States. According to a recent report, the global MMA market will reach 2.9 million metric tons by 2015. In a typical industrial process for producing MMA, a crude mixture containing MMA, methanol, and water is produced. Conventionally, separation of the mixture components is currently carried out using distillation. See, for example, U.S. Pat. No. 5,028,735 which teaches purification and preparation processes for methyl methacrylate in which a mixture containing water, methanol, and MMA as primary components along with at least one of methyl acrylate, methyl propionate, and methacrylic acid is azeotropically distilled together with hexane to obtain MMA in a form substantially free of water, methanol, methyl acrylate, methyl propionate and hexane and a low boiling point fraction, the latter of which is cooled and separated into a water phase and an oil phase. Methanol is recovered from the water phase by adding an alkaline substance and then distilling the resultant mixture. See also U.S. Pat. No. 5,435,892 which teaches a distillation process for separating methanol from a mixture of methanol with methyl acrylate or methyl methacrylate, as well as from a mixture of methanol and water with methyl acrylate or methyl methacrylate with the use of an azeotropic solvent, which forms an azeotropic mixture with methanol. One of the drawbacks of conventional distillation for separating and purifying MMA is that it is difficult and energy-intensive because the boiling point of MMA is close to that of water and methanol, as a result of which the MMA forms an azeotrope with them. The three-stage distillation technology currently employed in the industry for MMA purification requires a substantial amount of energy.

FIG. 1 shows an industrial three-column design flowsheet for a conventional three-stage azeotropic distillation process for MMA purification.

SUMMARY OF THE INVENTION

It is, thus, one object of this invention to provide a method and system for separating and purifying MMA which overcomes the disadvantages associated with conventional distillation processes.

This and other objects of this invention are addressed by a method for separating methyl methacrylate from a mixture containing said methyl methacrylate, methanol, and water in which the mixture is provided to a first stage membrane unit in which the mixture is dehydrated, producing a dehydrated mixture containing the methyl methacrylate and the methanol. The dehydrated mixture is provided to a second stage membrane unit in which the methanol is removed from the dehydrated mixture, producing a permeate stream containing primarily methanol (in a range of about 95% to about 100 wt %, preferably ≥99.9 wt %) and a retentate stream containing high purity (in a range of about 95% to about 100 wt %, preferably ≥99.9 wt %) methyl methacrylate. The benefits of this method compared with conventional azeotropic distillation technology include simpler processing and reduced energy consumption resulting in lower capital and operating costs, reduced carbon emissions due to the energy savings and no requirement for adding hydrocarbons, a smaller footprint and shorter height requirements, clearer end products due to a high separation factor that is not limited by vapor-liquid equilibrium, and design flexibility due to the modularity of membrane technology.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

Figure 1:
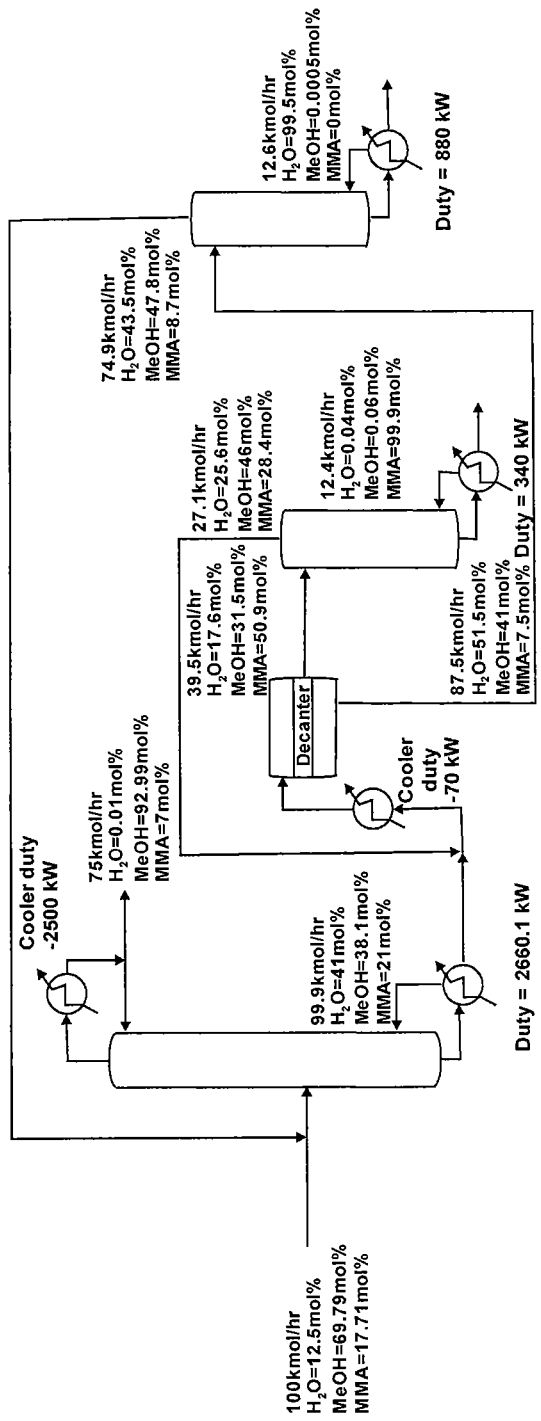
FIG. 1 is an industrial three-column design flowsheet for a conventional three-stage azeotropic distillation process for MMA purification.

The method of this invention employs an advanced two-stage molecular sieve membrane technology that can replace the currently employed three-stage azeotropic distillation process with improved energy efficiency and process intensification capabilities for dehydration and methanol recovery in the production of methyl methacrylate. The first stage is a dehydration step employing a first stage membrane unit having a small-pore hydrophilic molecular sieve membrane having high water selectivity which is applied in a pervaporation process for the removal of water from the crude MMA mixture. By small-pore membrane, we mean membranes having pore sizes in the range of about 0.35 nm (nanometers) to about 0.45 nm. Different from the currently used three-stage azeotropic distillation process, the pervaporation process employed in the method of this invention is not limited by vapor-liquid equilibrium. That is, pervaporation is able to separate azeotropes because the vapor-liquid equilibrium is not a controlling mechanisms for separations in membranes. In pervaporation, the feed is placed in contact with one side of a membrane while vapor permeate is removed from the opposite side of the membrane, which is maintained under a vacuum. The membrane, acting as a selective barrier between the two phases, allows the desired component(s) of the liquid feed to permeate through the membrane by vaporization. The driving force for transport through the membrane is the chemical potential gradient across the membrane. Pervaporation has other advantages over distillation, including reduced energy demand, because only a fraction of the liquid is vaporized, and relatively inexpensive equipment, because only a small vacuum pump is needed to create the driving force.

In accordance with one preferred embodiment of this invention, the crude MMA has a temperature in the range of about 60° C. to about 130° C.; pressure on the feed side of the membrane is in the range of about 0.1 to about 1000 psig; and pressure on the permeate side of the membrane, which is under vacuum, is in the range of about 0.5 kPa to about 30 kPa.

The membranes employed in the method of this invention are zeolite membranes and are of interest because they can separate liquid mixtures with high flux and separation factor due to their molecular-sized pores, preferential adsorption properties, and high porosity. They are also stable up to about 400° C. in a chemically corrosive environment. By high flux, we mean flux rates in the range of about 1 kg/m$^2$·h to about 10 kg/m$^2$·h and by high separation factor, we mean separation factors in the range of about 500 to about 100,000. By high porosity, we mean porosities in the range of about 20% to about 60%.

The second stage of the process of this invention is a methanol recovery process in which the water-depleted residue stream produced in the first stage of the process is sent to a polishing adsorption column to remove any remaining trace amounts of water in the stream following which the stream is provided to a second stage membrane unit in which methanol in the stream is recovered in the permeate stream and recycled to the reactor for producing MMA. The retentate stream in the second stage membrane unit is the purified product MMA.

The polishing adsorption column in accordance with one embodiment of this invention employs 3A zeolites having a pore diameter of about 0.3 nm as the column packing material. 3A zeolites adsorb only water from the retentate stream of the first stage membrane unit.

Figure 2:
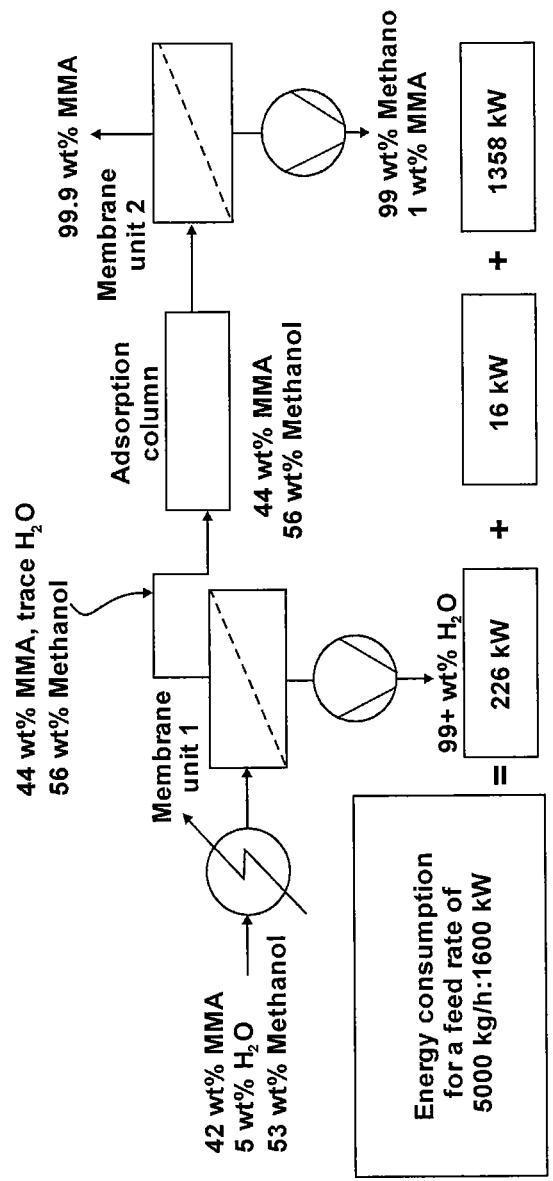
FIG. 2 is a process flow diagram for a membrane process for purifying MMA in accordance with one embodiment of this invention.

FIG. 1 shows a conventional three-stage azeotropic distillation process for MMA purification. As shown therein, total energy consumption for the process is about 6.45 MW. In contrast thereto, the process of this invention as shown in FIG. 2 has a total energy consumption of about 1.6 MW, less than 75% of the energy consumption of the conventional three-stage distillation process.

In accordance with one preferred embodiment of this invention, the first stage membrane unit utilizes a highly hydrophilic NaA membrane to separate water, which has a molecular diameter of about 0.26 nm, from methanol, which has a molecular diameter of about 0.39 nm, and MMA, which has a molecular diameter of about 0.63 nm, based on the differences in diffusivity and competitive adsorption. For a NaA membrane having a thickness of about 20 to about 30 mm, the flux rate is 2.5 kg/m$^2$·h and an H$_2$O/methanol separation factor of about 2200. NaA is a small-pore zeolite membrane having a pore size of about 0.42 nm and a composition of Na$_{12}$Al$_{12}$Si$_{12}$O$_{48}$•27H$_2$O.

Other small-pore hydrophilic zeolite membranes suitable for use in the first stage membrane unit include, but are not limited to, SAPO-34 and ALPO-18 membranes. SAPO-34, which has a CHA structure and a 0.38 nm pore diameter, is a silicoaluminophosphate having the composition Si$_x$Al$_y$P$_z$O$_2$, where x=0.01-0.98, y=0.01-0.60, and z=0.01-0.52. The SAPO-34 structure is formed by substituting silicon for phosphorus in AlPO$_4$ which has a neutral framework and exhibits no ion exchange capacity.

Microporous aluminophosphates (AlPOs) are a class of zeolites with structures built of AlO$_4^-$ and PO$_4^-$ tetrahedral building units. In particular, AlPO-18 has a structure of AEI. The AEI framework topology of this aluminophosphate is characterized by a three-dimensional framework possessing eight membered intersecting channels with a diameter of about 0.38 nm.

In accordance with one preferred embodiment of this invention, the second stage membrane unit utilizes a FAU membrane, which has a pore size of about 0.74 nm as measured by x-ray diffraction (XRD), for methanol recovery. FAU membranes have a structure of faujasite, which is a large-pore zeolite framework, and include zeolites X and Y. The typical chemical composition of zeolite X is Na$_2$O•Al$_2$O$_3$•2.5SiO$_2$•6H$_2$O whereas the typical chemical composition of zeolite Y is Na$_2$O•Al$_2$O3•4.8SiO2•8.9H$_2$O. FAU zeolites are used commercially as an adsorbent and as a catalyst. The framework is stable and rigid and contains a void space that is about 50% of the dehydrated crystal volume. FAU membranes are strongly hydrophilic.

Other large-pore hydrophilic zeolite membranes suitable for use in the method of this invention include, but are not limited to, zeolite T and mordenite membranes. By large-pore, we mean pore sizes in the range of about 0.55 to about 0.80 nm. Zeolite T membranes have an OFF structure, a pore diameter of 0.68 nm as measured by XRD, and Si/Al ratio of about 3.6. Mordenite membranes have a MOR structure and an Si/Al ratio of about 5. Mordenite has an ordered distribution of Si and Al in the framework structure. The structure consists of two major channels—one (0.65×0.70 nm pores) having 12 oxygen atoms and the other (0.26×0.57 nm pores) having 8 oxygen atoms.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for separating methyl methacrylate from a mixture containing said methyl methacrylate, methanol, and water comprising the steps of:
   providing said mixture to a first stage membrane unit in which said mixture is dehydrated, producing a dehydrated mixture containing said methyl methacrylate and said methanol; and
   providing said dehydrated mixture to a second stage membrane unit in which said methanol is removed from said dehydrated mixture, producing a permeate stream containing said methanol and a retentate stream containing in a range of about 95% to about 100 wt % said methyl methacrylate;
   wherein the first stage membrane unit comprises a small-pore hydrophilic membrane having a thickness of greater than about 20 μm and pore sizes of about 0.35 to about 0.45 nanometers selected from the group consisting of the following, and combinations thereof:
   a) Na$_{12}$Al$_{12}$Si$_{12}$O$_{48}$•27H$_2$O,
   b) Si$_x$Al$_y$P$_z$O$_2$, where x=0.01-0.98, y=0.01-0.60, z=0.01-0.52,
   c) microporous aluminophosphates; and
   the second stage membrane unit comprises a hydrophilic membrane having a faujasite structure.

2. The method of claim 1, wherein said dehydrated mixture is provided to a polishing adsorption column in which any remaining trace amounts of water are removed.

3. The method of claim 1, wherein said first stage membrane unit comprises a hydrophilic zeolite A membrane.

4. The method of claim 1, wherein said second stage membrane unit comprises a zeolite FAU membrane.

5. The method of claim 2, wherein said polishing adsorption column contains a column packing material comprising 3A zeolites.

6. The method of claim 1, wherein said methanol is recycled to a methyl methacrylate production process.

7. A method for separating the components of a mixture containing methyl methacrylate, water, and methanol comprising the steps of:
dehydrating said mixture in a first stage membrane unit, producing a dehydrated mixture; and removing said methanol from said dehydrated mixture in a second stage membrane unit, producing a retentate stream containing said methyl methacrylate and 5.0 wt % said methanol;
wherein the first stage membrane unit comprises a small-pore hydrophilic membrane having pore sizes of about 0.35 to about 0.45 nanometers selected from the group consisting of the following, and combinations thereof:
a) $Na_{12}Al_{12}Si_{12}O_{48} \cdot 27H_2O$,
b) $Si_xAl_yP_zO_2$, where x=0.01-0.98, y=0.01-0.60, z=0.01-0.52,
c) microporous aluminophosphates; and
the second stage membrane unit comprises a hydrophilic membrane having a faujasite structure.

8. The method of claim 7, wherein said first stage membrane unit comprises a hydrophilic zeolite A membrane.

9. The method of claim 7, wherein said second stage membrane unit comprises a zeolite FAU membrane.

10. The method of claim 7, wherein said dehydrated mixture is provided to a polishing adsorption column in which any remaining trace amounts of said water are removed.

11. The method of claim 10, wherein said polishing adsorption column contains a column packing material comprising 3A zeolites.

12. The method of claim 7, wherein at least a portion of said methanol removed from said dehydrated mixture is recycled for use in the production of said methyl methacrylate.

13. The method of claim 7, wherein the small-pore hydrophilic membrane has a thickness of greater than about 20 µm.

* * * * *